United States Patent
Hauptmann et al.

(10) Patent No.: US 6,713,421 B1
(45) Date of Patent: Mar. 30, 2004

(54) BLANK COMPRISED OF A ZIRCONIUM OXIDE CERAMIC WITH AN OXIDE ADDITIVE AND THE USE THEREOF

(75) Inventors: Holger Hauptmann, Sindelsdorf (DE); Robert Schnagl, Landsberg (DE); Sybille Frank, Seefeld (DE)

(73) Assignee: 3M ESPE AG, Seefeld (DE)

(*) Notice: Subject to any disclaimer, the term of this patent is extended or adjusted under 35 U.S.C. 154(b) by 35 days.

(21) Appl. No.: 10/049,661

(22) PCT Filed: Aug. 16, 2000

(86) PCT No.: PCT/EP00/07991
§ 371 (c)(1),
(2), (4) Date: Apr. 11, 2002

(87) PCT Pub. No.: WO01/12132
PCT Pub. Date: Feb. 22, 2001

(30) Foreign Application Priority Data

Aug. 16, 1999 (DE) .......................................... 199 38 143

(51) Int. Cl.⁷ ............................................. C04B 35/486
(52) U.S. Cl. .................... 501/103; 501/105; 433/202.1; 433/212.1
(58) Field of Search ................ 501/103, 105; 106/35; 433/202.1, 212.1

(56) References Cited

U.S. PATENT DOCUMENTS

| 5,219,805 A | * | 6/1993 | Yoshida et al. .............. 501/103 |
| 5,263,858 A | * | 11/1993 | Yoshida et al. ................. 433/8 |
| 5,453,227 A | * | 9/1995 | Rieger ........................ 264/40.1 |
| 5,656,564 A | * | 8/1997 | Nakayama et al. .......... 501/103 |
| 6,087,285 A | * | 7/2000 | Oomichi et al. ............. 501/103 |
| 6,358,874 B1 | * | 3/2002 | Kobayashi et al. .......... 501/105 |

FOREIGN PATENT DOCUMENTS

| DE | 42 07 179 A1 | 9/1992 |
| EP | 0 634 149 A1 | 1/1995 |
| EP | 0 908 425 A1 | 4/1999 |
| JP | 11 116328 A | 4/1999 |

OTHER PUBLICATIONS

Kosmac et al., J Biomed Mater Res, vol. 53, No. 4, pp. 304–313 Feb. 2000.

* cited by examiner

Primary Examiner—Karl Group
(74) Attorney, Agent, or Firm—Birch, Stewart, Kolasch & Birch, LLP

(57) ABSTRACT

The invention relates to blanks comprising zirconium oxide-based ceramic with an addition of 0.1 to 0.50 wt.-% of at least one of the oxides of the elements aluminium, gallium, germanium, indium and their use.

7 Claims, No Drawings

BLANK COMPRISED OF A ZIRCONIUM OXIDE CERAMIC WITH AN OXIDE ADDITIVE AND THE USE THEREOF

This application is the national phase under 35 U.S.C. §371 of PCT International Application No. PCT/EP00/07991 which has an International filing date of Aug. 16, 2000, which designated the United States of America.

The invention relates to blanks for the preparation of dentures made from zirconium oxide ceramic with oxidic additive. In particular, the invention relates to blanks made from zirconium oxide ceramic which were reacted with 0.1 to 0.50 wt.-% of at least one of the oxides of the elements aluminium, gallium, germanium, indium, for the preparation of dentures, in particular crowns and bridges.

The use of ceramic prostheses in dentistry represents a desirable goal, as ceramic materials are characterized by high strengths and, unlike metal prostheses, already have tooth colour or assume it after firing. Because of the high tissue compatibility and the low heat conductivity compared with metals, ceramics are particularly suitable for dentures.

Pure zirconium oxide cannot be used for mechanical applications as its volume changes too much through modification changes during the cooling process after sintering. Through the addition of magnesium, cerium or yttrium oxides, however, this process can be checked. A detailed discussion can be found in "Aluminium-und Zirkonoxidkeramik in der Medizin" [Aluminium and Zirconium Oxide Ceramics in Medicine], reprint from Industrie Diamanten Rundschau, IDR 2/1993 and also in EP-A-0 634 149.

EP-A-0 630 622 describes zirconium oxide-based blanks which, in addition to the constituents hafnium and yttrium oxide which are unavoidable when using zirconium oxide, contain up to 0.2 wt.-% impurities.

In EP-A-0 634 149, similar compositions are described in which the proportion of impurities is said to be under 0.1 wt.-%.

The disadvantage of impurities is the inclination, caused by the latter, of the ceramics to form glass or glass phases during the sintering process. Impurities therefore ultimately have a negative effect on the strength of the denture parts prepared from these ceramics and should be unconditionally avoided.

The object of the invention is to provide blanks for the preparation of fracture-resistant and accurately-fitting dentures.

Surprisingly, it was found that blanks, comprising zirconium oxide-based ceramics with an addition of 0.1 to 0.50 wt.-% of at least one of the oxides of the elements aluminium, gallium, germanium, indium are suitable for the preparation of complex dentures and filigree structures. Preferably, the oxides of the abovementioned elements are present in an amount as defined above with homogeneous distribution and not, like the impurities, unevenly and with varying concentration distribution. This homogeneous distribution can be achieved for example through co-precipitation as described in the embodiment of this invention.

Moreover, a uniform distribution of the particles formed during a pre-sintering process is advantageous. The granular form of the particles is preferably equiaxial with an average grain diameter of less than 1 $\mu$m, particularly preferably less than 0.7 $\mu$m.

Blanks according to the invention usually have a pore volume of 50 to 65%. The average pore size usually lies in the range from 3 $\mu$m to 0.1 $\mu$m, the range from 2 $\mu$m to 0.2 $\mu$m being preferred.

The blanks according to the invention comprise ceramics containing the components of the composition (1) described hereafter:

(A) 91 to 98.40 wt.-%, preferably 91 to 97.25 wt.-% zirconium oxide, (B) 0 to 3.5 wt.-%, preferably 0 to 2.5 wt.-% hafnium oxide, (C) 1.5 to 6.0 wt.-%, preferably 2.5 to 6.0 wt.-% yttrium oxide, (D) 0.1 to 0.50 wt.-%, preferably 0.15 to 0.50 wt.-%, particularly preferably 0.20 to 0.50 wt.-%, quite particularly preferably 0.25 to 0.50 wt.-% of at least one of the oxides of the elements aluminium, gallium, germanium, indium, (E) 0 to 1.9 wt.-%, preferably 0.0005 to 1.5 wt.-% coloring additives.

The sum of the wt.-% of the components (A) to (E) must add up to 100.

By component (E) of the composition (1) are meant coloring oxides from elements of the group Pr, Er, Fe, Co, Ni, Ti, V, Cr, Cu, Mn, with $Fe_2O_3$, $Er_2O_3$ or $MnO_2$ preferably being used.

Moreover, the blanks according to the invention have a particularly high and uniformly distributed hardness and strength which makes them eminently suitable for use in the preparation of high-quality dentures by working of blanks in the non-densely sintered state.

As a homogeneous distribution of hardness and strength as well as density within each spatial direction of the non-densely sintered blank is required, it is advantageous that, through the use of the blanks according to the invention, even very small deviations in the density and hardness distribution of the non-densely sintered ceramic are avoided.

This is particularly advantageous when filigree structures or multisection bridges are to be prepared, as even very small inhomogeneities lead to breaking points which considerably impair the durability of these complex structures during working or lead to a different sintering behaviour which can be recognized from the distortion of the workpiece.

The addition of 0.1 to 0.50 wt.-%, preferably 0.15 to 0.50 wt.-%, particularly preferably 0.20 to 0.50 wt.-%, quite particularly preferably 0.25 to 0.50 wt.-% of at least one of the oxides of the elements aluminium, gallium, germanium, indium to such ceramics leads to the lowering of the sintering temperature and the increasing of the stability and the hydrolytic resistance in the densely sintered state. This situation is to be found for aluminium oxide in "Zirconia Powder" 09/97 product information from the company Tosoh.

The use of the powder named there for the preparation of accurately-fitting dentures is not mentioned. Its suitability for the intended use according to the invention is more, rather-than less, surprising because, as stated previously, it had to be assumed that foreign oxides represent impurities which negatively influence the breaking resistance and must be avoided.

The composition (1) according to the invention is prepared by dissolving the components (A) and (B) of the composition (1) contained in commercially available zirconium sand with HCl, mechanically separating the low-soluble impurities and combining them with the additives (C) and (D) likewise present as oxichlorides or chlorides after treatment with HCl as an aqueous, strongly acid solution.

Additives according to component (E) acting as colorants are then added likewise as chlorides, obtained through dissolution in HCl.

There follows a co-precipitation of the dissolved components by hydrolysis, calcination of the precipitation product, grinding of the calcinate to the desired end fineness and also a spray-drying process using temporary slip and binding agents.

The blanks according to the invention are converted, using known compression moulding processes, from the granules obtained in this manner into the desired preform, for example cylinders. These mouldings are released from the binder by a binder-dependent heat treatment and pre-sintered at a temperature between 850° C. and 1000° C., preferably between 950° C. and 995 ° C. with 0.5 to 2 hours holding time.

The blanks worked using customary processes, for example CAD/CAM or profiling, are densely sintered for example at 1200° C. to 1650° C., particularly preferably 1350° C. to 1550° C.

In particular the presence of impurities in the composition given above of the blanks according to the invention encourages the formation of glass phases or glass during the sintering process. Preferred according to the present invention are therefore compositions which allow a generation of blanks which do not form any glass phases or glass during the densifying.

The blanks according to the invention furthermore display a preferred deviation from the linearity of the shrinkage per spatial direction which is less than 0.05%, particularly preferably less than 0.01%.

It is furthermore known that the strength of nonmetallic-inorganic systems in general depend on the critical stress intensity factor $K_{IC}$. This factor is clearly lower with amorphous materials, for example glasses, than with purely crystalline systems (D. Munz/T. Fett: Mechanisches Verhalten keramischer Werkstoffe [Mechanical Behaviour of Ceramic Materials], Springer-Verlag). Thus the strength of ceramics also decreases if amorphous phases form at the grain boundaries. The ceramics preferably usable according to the invention therefore display for example a $K_{IC}$ value of 5 to 10, preferably 8 to 10, measured according to EN 843.

The invention is explained in more detail in the following by means of examples without thereby being limited in any way.

Strength data, in particular breaking resistances within the framework of these statements, relate to the "piston-on-three-ball test" according to ISO 6872.

The disclosed zirconium oxide ceramics can be used to particular advantage within the framework of the process described in DE-199 38 144 for the preparation of dentures with presintered blanks.

The subject-matter of the invention is therefore also devices which contain at least one blank according to the invention. By devices are meant for example open or closed blank holding devices.

To prepare the blanks according to the invention, preforms obtained while applying pressure are taken as a basis. When preparing these preforms, examples of starting materials are pure chlorides, oxichlorides or nitrates, chlorides being used in the examples.

PREPARATION EXAMPLES 1 AND 2

Zirconium Oxide Ceramic Containing Aluminium Oxide

To obtain approx. 200 g of ready doped compressed granules, the components are dissolved in distilled water according to the following table:

| No. | $M(ZrCl_4)$ [g] | $M(YCl_3 \cdot 6H_2O)$ [g] | $M(AlCl_3)$ [g] | $M(FeCl_3)$ [g] | $M(ErCl_3)$ [g] |
|---|---|---|---|---|---|
| 1 [coloured] (% as oxide) | 355.6 (94.0) | 33.4 (5.17) | 0.65 (0.25) | 0.77 (0.2) | 0.29 (0.38) |
| 2 [un-coloured] (% as oxide) | 357.66 (94.55) | 33.36 (5.20) | 0.65 (0.25) | 0 | 0 |
| Component | (A) | (C) | (D) | (E) | (E) |

There follows a co-precipitation of the dissolved components by hydrolysis, the aforementioned solution being reacted with 32 l 6-molar aqueous $NH_4OH$ solution. An at least 30-times excess of $OH^-$ concentration relative to the stochiometric requirement is recommended. The precipitation product must then be washed free of $Cl^-$. The calcination of the precipitation product is carried out at 700° C. over 0.75 hours, followed by a grinding of the calcinate to an end fineness of $D_{50}=0.6$ μm and also by a spray-drying process using temporary slip and binding agents (here: 2.0 wt.-% PVA, 0.15 wt.-% oleic acid relative to oxide).

Using an isostatic press, for example at 1500 to 2500, preferably 1700 to 2200 bar, the granules obtained are made into preforms measuring d=31 mm and I=150 mm.

The preforms are released by a heat treatment (heating rate: 4 K/min to 650° C., 1 hour holding time) and presintered at a temperature of 970° with 0.5 hours holding time to produce the blanks according to the invention.

Process Examples

To prepare accurately-fitting bridges, blanks prepared according to the preparation examples 1 and/or 2 are worked with a CAD/CAM system by milling or grinding and densely sintered under the following parameters, for example with the aid of a device from DE-199 04 534:

Heating rate: 10K/min to final temperature: 1 500° C. Holding time at final temperature: 2 h the result is in both cases extremely accurately-fitting dentures with a high breaking resistance (σ>1000 Mpa).

What is claimed is:

1. A blank comprising zirconium oxide-based ceramic, containing:
   (A) at least 91 wt.-% zirconium oxide,
   (B) 0 to 3.5 wt.-% hafnium oxide,
   (C) 1.5 to 6.0 wt.-% yttrium oxide,
   (D) 0.15 to 0.50 wt.-% of at least one of the oxides of the elements aluminum, gallium, germanium, and indium,
   (E) 0.2 to 1.5 wt.-% coloring additives, selected from the group consisting of the oxides $Fe_2O_3$, $Er_2O_3$ and $MnO_2$, wherein the wt.-% must add up to 100.

2. The blank according to claim 1, containing:
   (A) 91 to 97.25 wt.-% zirconium oxide,
   (B) 0 to 2.5 wt.-% hafnium oxide,
   (C) 2.5 to 6 wt.-% yttrium oxide,
   (D) 0.15 to 0.50 wt.-% aluminum oxide,
   (E) 0.2 to 1.5 wt.-% coloring additives, selected from the group consisting of the oxides $Fe_2O_3$, $Er_2O_3$ and $MnO_2$, wherein the wt.-% must add up to 100.

3. The blank according to claim 1, containing:
   (A) 91 to 98.20 wt.-% zirconium oxide,
   (B) 0 to 2.5 wt.-% hafnium oxide,
   (C) 1.5 to 6.0 wt.-% yttrium oxide,
   (D) 0.25 to 0.50 wt.-% aluminum oxide,
   (E) 0.2 to 1.5 wt.-% coloring additives, selected from the group consisting of the oxides $Fe_2O_3$, $Er_2O_3$ and $MnO_2$.

4. A method for preparing a blank comprising zirconium oxide-based ceramic, said method comprising the steps of:
   (1) preparing a powder or granules containing:
      (A) at least 91 wt.-% zirconium oxide,
      (B) 0 to 3.5 wt.-% hafnium oxide,
      (C) 1.5 to 6.0 wt.-% yttrium oxide,
      (D) 0.15 to 0.50 wt.-% of at least one of the oxides of the elements aluminum, gallium, germanium, and indium,
      (E) 0.2 to 1.5 wt.-% coloring additives, selected from the group consisting of the oxides $Fe_2O_3$, $Er_2O_3$ and $MnO_2$,
   wherein in which the wt.-% must add up to 100,
   (2) molding the granules or powder by applying pressure to produce preforms,
   (3) treating the performs With heat to produce the blank.

5. A device comprising at least one blank according to at least one of claims 1 to 3.

6. A denture having a structure wherein at least a portion of the structure comprises a zirconium oxide-based ceramic, containing:
   (A) at least 91 wt.-% zirconium oxide,
   (B) 0 to 3.5 wt.-% hafnium oxide,
   (C) 1.5 to 6.0 wt.-% yttrium oxide,
   (D) 0.15 to 0.50 wt.-% of at least one of the oxides of the elements aluminum, gallium, germanium, and indium,
   (F) 0.2 to 1.5 wt.-% coloring additives, selected from the group consisting of the oxides $Fe_2O_3$, $Er_2O_3$ and $MnO_2$,
   wherein the wt.-% must add up to 100.

7. The denture according to claim 6, containing:
   (A) 91 to 97.25 wt.-% zirconium oxide,
   (B) 0 to 2.5 wt.-% hafnium oxide,
   (C) 2.5 to 6 wt.-% yttrium oxide,
   (D) 0.15 to 0.50 wt.-% aluminum oxide,
   (E) 0.2 to 1.5 wt.-% coloring additives, selected from the group consisting of the oxides $Fe_2O_3$, $Er_2O_3$ and $MnO_2$,
   wherein the wt.-% must add up to 100.

* * * * *

UNITED STATES PATENT AND TRADEMARK OFFICE
CERTIFICATE OF CORRECTION

PATENT NO. : 6,713,421 B1
DATED : March 30, 2004
INVENTOR(S) : Hauptmann, Holger It is certified that error appears in the above-identified patent and that said Letters Patent is hereby corrected as shown below:

Column 2,
Line 56, delete "rather-than" and insert -- rather than --, therefore.

Column 3,
Line 15, delete "995 ° C" and insert -- 995° C --, therefore.

Column 4,
Line 43, delete "1 500° C" and insert -- 1500° C --, therefore.
Line 45, delete "the" and insert -- The --, therefore.

Column 5,
Line 23, "wherein" delete "in which".
Line 26, delete "performs" and insert -- performs --, therefore.
Line 26, delete "With" and insert -- with --, therefore.

Signed and Sealed this

Twenty-eighth Day of June, 2005

JON W. DUDAS
*Director of the United States Patent and Trademark Office*